(12) United States Patent
Maki

(10) Patent No.: US 6,589,233 B1
(45) Date of Patent: Jul. 8, 2003

(54) LASER IRRADIATION APPARATUS

(75) Inventor: Shin Maki, Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 56 days.

(21) Appl. No.: 09/635,776

(22) Filed: Aug. 11, 2000

(30) Foreign Application Priority Data

Aug. 12, 1999 (JP) .......................................... 11-228930

(51) Int. Cl.$^7$ ............................................. A61B 18/20
(52) U.S. Cl. ........................... 606/17; 606/10; 606/13; 606/15
(58) Field of Search ...................... 606/2, 3, 7, 10–17

(56) References Cited

U.S. PATENT DOCUMENTS

| | | | |
|---|---|---|---|
| 4,819,632 A | * | 4/1989 | Davies ........................... 606/7 |
| 4,932,956 A | | 6/1990 | Reddy et al. |
| 4,932,958 A | | 6/1990 | Reddy et al. |
| 5,207,672 A | | 5/1993 | Roth et al. |
| 5,292,320 A | | 3/1994 | Brown et al. |
| 5,451,221 A | * | 9/1995 | Cho et al. ....................... 606/7 |
| 5,496,308 A | | 3/1996 | Brown et al. |
| 5,916,210 A | * | 6/1999 | Winston ........................ 606/7 |

FOREIGN PATENT DOCUMENTS

| | | | |
|---|---|---|---|
| EP | 0 673 627 | 9/1995 | |
| FR | 2637492 | * 10/1988 | .................... 606/7 |
| WO | 92/04934 | 4/1992 | |
| WO | 93/04727 | 3/1993 | |

* cited by examiner

*Primary Examiner*—David M. Shay
(74) *Attorney, Agent, or Firm*—Burns, Doane, Swecker & Mathis, LLP

(57) ABSTRACT

The laser irradiation apparatus 100 comprises: a long and slender main body 101; a rotating shaft 180 that is held, rotatably inside the main body 101; optical fibers 103a, 103b; multiple reflecting mirrors 181a–181f that are installed on the rotating shaft 180 and reflect the laser rays; and a drive unit 105 that drives the rotating shaft. Multiple reflecting mirrors 181a14 181f are located in different positions along the longitudinal and circumferential directions of the rotating shaft 180. The slanting angles of reflecting mirrors 181a14 181f move are set at angles that converge the reflected laser rays at a target area. The positions where reflecting mirrors 181a14 181f reflect the laser rays move along the axial direction as the rotating shaft 180 rotates. The vicinity of the target area is maintained at relatively low temperatures. In the meanwhile, the target area is heated to a specified temperature due to the convergent of the laser rays.

14 Claims, 6 Drawing Sheets

LASER IRRADIATION APPARATUS

This application is based on patent application Ser. No. 11-228930 filed on Aug. 12, 1999 in Japan, the content of which is hereby incorporated by reference.

BACKGROUND OF THE INVENTION

1. Field of the Invention

This invention relates to a laser irradiation apparatus, in particular, a laser irradiating medical apparatus for treating tumors such as cancer, benign prostatic hyperplasia, etc., by irradiating vital tissues with laser rays, said apparatus being left in vital tissues by means of insertion into vital lumens such as blood vessels, urethras, and abdominal cavities or by means of puncturing organs.

2. Description of the Related Art

A technique of treating lesions by means of laser irradiation apparatuses has been known. The long and slender main body of a laser irradiation apparatus is inserted into a body cavity or a lumen formed by small discission. Lesion tissues are diminished or cleared through alteration, sphacelation, coagulation, cauterization and evaporation by means of irradiating the lesions with laser rays.

The technique is generally to irradiate directly a lesion existing on the surface layer of a vital tissue or its vicinity. However, in order to apply this technique to a deep lesion, heating the lesion to a sufficient temperature, it is necessary to irradiate it with a laser ray of a relatively high power. As a result, there may be a case of or a concern for damaging normal tissues adjacent to the lesion, such as the surface layer.

WO93/04727 discloses a technique for coagulating and diminishing a part of a tumor or prostate by means of laser irradiation. This technique is to infuse a coolant into a balloon in order to heat only the internal tumor or the prostate without heating the surface of the urethra that is adjacent to the balloon. Laser ray is irradiated from a fixed laser irradiator in this case. Consequently, it is necessary to use a low-power laser ray so as not to heat the surface of the urethra, thus requiring a long irradiation time.

U.S. Pat. No. 5,292,320 disclosed an apparatus for treating benign prostatic hyperplasia transurethrally using laser rays. In this apparatus, multiple irradiation units placed at different positions irradiates laser rays simultaneously. The irradiated laser rays are converged on a target point in a deep legion to generate a sufficient heat for heating and diminishing the legion tissue. Consequently, the temperature in the vicinity of the target point becomes higher than other parts where the laser rays do not converge. However, since the light paths of the laser rays are fixed, certain areas are formed where the temperatures are slightly higher than normal in the vicinity of the surface layer where no conversions of laser rays are occurring. This phenomenon provides an ill affect on the protection of the surface. Therefore, it is not satisfactory from the point of treating only a deep lesion while preventing damages on the surface layer.

SUMMARY OF THE INVENTION

The object of this invention is to provide an apparatus that effectively irradiates a target area with laser rays, particularly a target area hidden deep inside a vital tissue, while securely preventing damages to normal tissues, particularly, a normal surface tissue that is in contact with the laser irradiation apparatus.

In one aspect of the invention, it is a laser irradiation apparatus, comprising:

a long and slender main body;

a rotating shaft that is held rotatably inside the main body;

an optical fiber provided inside the main body to guide the laser rays;

multiple laser ray emitting parts that are provided on the rotating shaft to reflect the laser rays guided by the optical fiber; and a drive unit for providing rotation to the rotating shaft, wherein the multiple emitting parts are arranged on different locations on the rotating shaft along the longitudinal and circumferential directions.

According to the laser irradiation apparatus, it is possible to effectively irradiate the target area hidden deep inside the tissue with laser rays, while preventing easily and securely damages to normal tissues, particularly, the normal tissues which are in contact with the apparatus.

In another aspect of the invention, the laser ray emitting parts are provided to be movable along the longitudinal direction of the rotating shaft and the apparatus further comprises a traveling unit that causes the emitting parts to travel in the longitudinal direction of the rotating shaft.

With such a constitution, it is possible to adjust the depth of a specific area where the laser rays reflected by the emitting part converge.

The objects, features and characteristics of this invention other than those set forth above will become apparent from the description given herein below with reference to preferred embodiments illustrated in the accompanying drawings.

DETAILED DESCRIPTION OF THE PREFERRED EMBODIMENT

The laser irradiation apparatus based on this invention will be described in detail below referring to some preferable embodiments.

Embodiment 1

Figure 1:
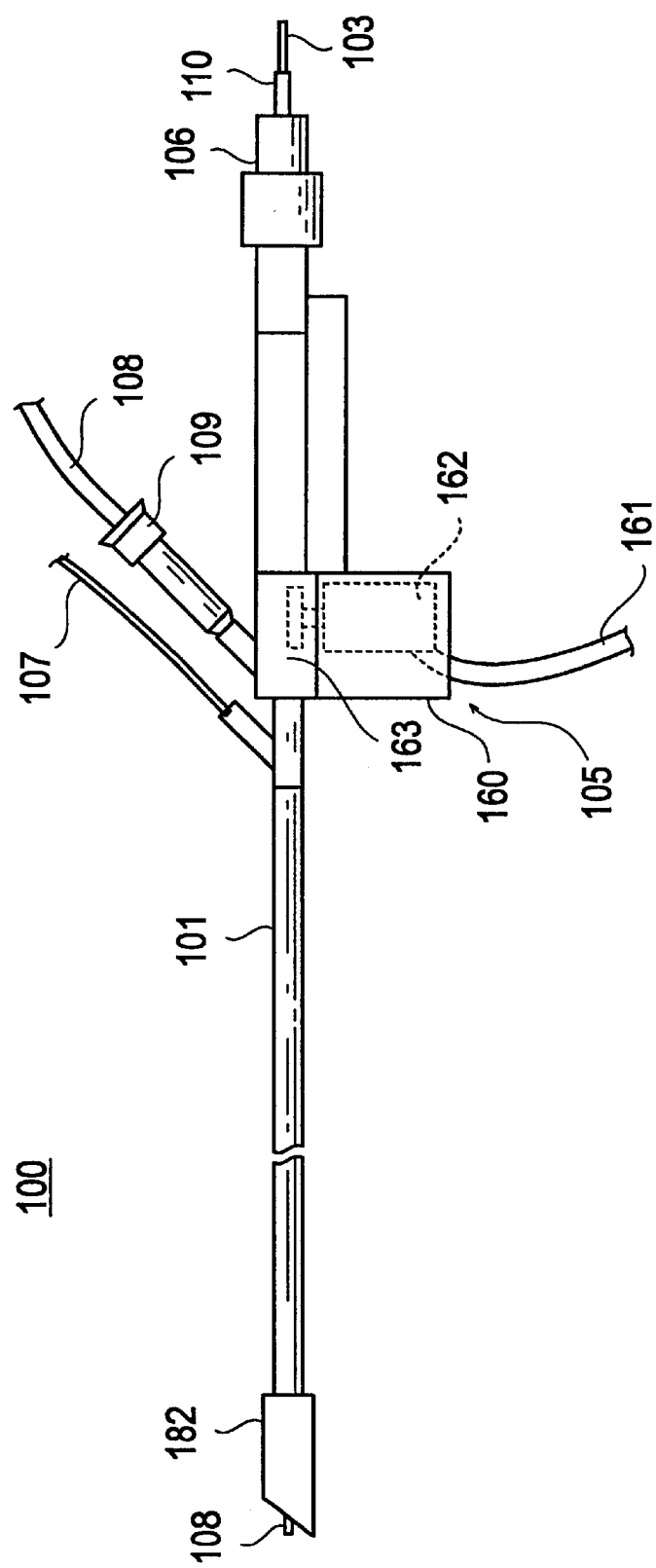
FIG. 1 is a perspective view of a laser irradiation apparatus according to a first embodiment of the present invention.
Figure 2:
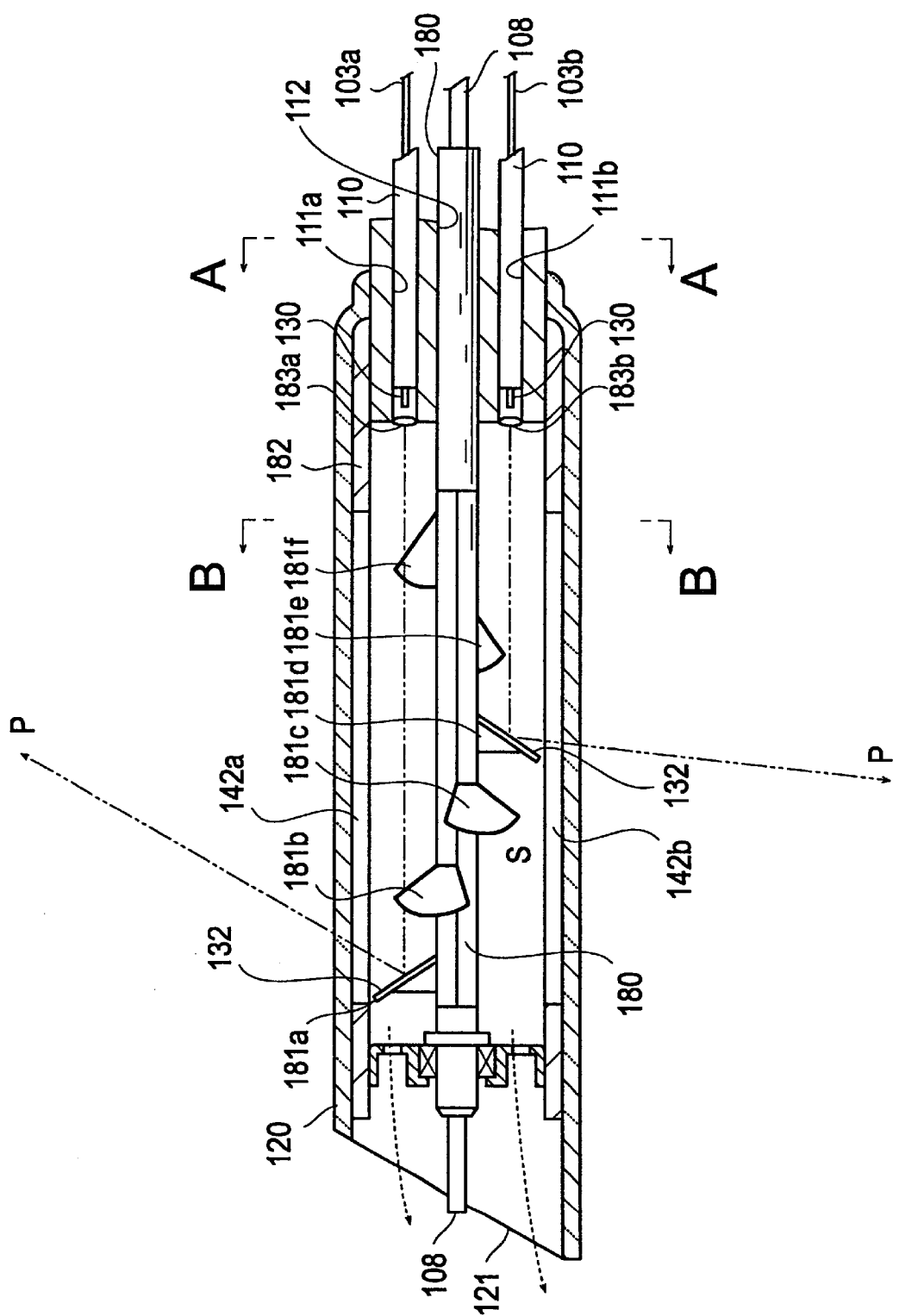
FIG. 2 is a cross-sectional view of the distal end of the laser irradiation apparatus of the first embodiment.

Refer to FIG. 1 and FIG. 2, the laser irradiation apparatus 100 according to the first embodiment is a sideway irradiation type one that irradiates vital tissues with laser rays, which is used, for example, for the benign prostatic hyperplasia treatment.

The laser irradiation apparatus 100 comprises: a long and slender main body 101 made of a tube-like member; a rotating shaft 180 that is held rotatably inside the main body 101; optical fibers 103 (collective name for 103a and 103b) that are installed in the main body 101 and guide laser rays received at its proximate end; multiple emitting parts 181 (collective name for 181a–181f) that are installed on the rotating shaft 180 and reflect the laser rays guided by the optical fibers 103; and a drive unit 105 that drives the rotating shaft 180. Multiple emitting parts 181 are located in different positions along the longitudinal and circumferential directions of the rotating shaft 180.

The optical fiber 103 is gripped and affixed by a distal end 106 of the laser irradiation apparatus 100.

In order to cool the surface of the vital tissue which is irradiated by the laser rays, the emitting end of the optical fiber 103, and the emitting part 181, cooling water is supplied to the main body 101 via a cooling water supply tube 107 from a coolant supply device (not shown).

The proximal end of the laser irradiation apparatus 100 is provided with an insertion port 109 for the endoscope 108. The endoscope 108 is inserted into the main body 101 through the insertion port 109 in such a way as to be able to move in and out freely.

More specifically, the distal end of the main body 101 is connected to a housing 182 that holds the distal end of the rotating shaft 180 rotatably as shown in FIG. 2. The housing 182 consists of a hard tube-like member and has laser ray emitting windows 142 (collective name for 142a and 142b) at upper and lower positions in the drawing. The housing 182 is covered by a protective cover 120 made of a light transmitting material. The laser rays pass through the emitting windows 142 and the protective cover 120 and irradiate on the lesions. The distal ends of the housing 182 and the protective cover 120 are opened. The distal end of the protective cover 120 is formed into a slant face 121 in order to make it easier to insert it into the living body.

Figure 3:
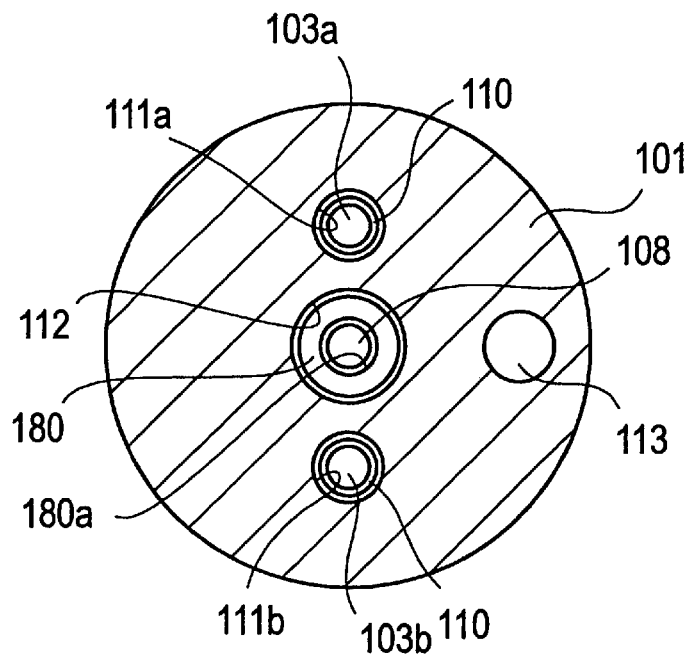
FIG. 3 is a cross-sectional view along the line A—A of the laser irradiation apparatus shown in FIG. 2.

As shown in FIG. 3, lumens 111a and 111b, through which optical fibers 103a and 103b covered with the protective tube 110 are inserted; lumen 112, through which rotating shaft 180 is rotatably inserted; and a lumen 113 that communicates with the cooling water supply tube 107 and guides the cooling water into the housing 182 are formed in the main body 101. All of these lumens, 111a, 111b, 112, and 113 are formed parallel to the axis of the main body 101. The endoscope 108 is inserted into a center hole 180a of the rotating shaft 180 in such a way as to be able to move in and out. Having passed through the lumen 113, the cooling water flows into the space S (see FIG. 2) in the housing 182 through the end of the lumen 113. The cooling water flows through the housing 182 and flows out from the open end of the protective cover 120 into a bladder as shown in FIG. 2 with dotted arrows. Heating at the distal end 130 of the fiber and the emitting part 181 can be suppressed by such a flow of the cooling water. Moreover, it is possible to cool normal tissues that are in contact with the protective cover 120 and heat only the deep area more safely.

It is also possible to close the distal end of the protective cover 120, form a lumen to discharge the cooling water into the main body 101, and circulate the cooling water in the housing 182.

In order to prevent the cooling water from leaking, O-rings (not shown) are provided to seal the gaps between the protective tube 110 and the lumens 111a and 111b. It is preferable to prevent the cooling water from flowing backwards by means of providing a check valve (not shown) in the cooling water guiding lumen 113. The temperature of the coolant is not particularly specified as long as it can reduce damages on the surface of the vital tissues and at the distal end 130 of the fiber and the emitting part 181, but it is preferably 0–37° C. The temperature of the coolant should preferably be 8–25° C., which can rarely cause frostbite and still provide a sufficient cooling effect. The cooling water should be a disinfected liquid, preferably a distilled water or a physiological saline.

The endoscope 108 has an optical fiber bundle, which guides an image, an optical fiber, which guides an illuminating light, and a protective tube, which integrally covers the optical fiber bundle and the optical fiber. The endoscope 108 has an image formation lens (not shown) at the distal end. The positioning of the housing 182 and the confirmation of the laser irradiation position can be visually done by means of endoscopic observation.

In the first embodiment, the optical fibers 103a and 103b are arranged at two different positions on a circumference about the rotating shaft 180. More specifically, they are located at upper and lower positions in the drawing, diametrically apart to each other. The optical fibers 103a and 103b are inserted into the lumens 111a and 111b respectively to transmit the laser rays. Each optical fiber 103 is totally covered, except its distal end, by the protective tube 110. The proximate end of the optical fiber 103 is connected to a laser generator (not shown) via an optical connector. Although the rotating shaft 180 rotates, the optical fiber 103 does not rotate. During the irradiation of the laser, the optical fibers 103 do not slide within the lumens 111a and 111b, and the distal ends 130 of the fiber are positioned at the respective distal end of the lumen 111a and 111b.

Next, it is described the structure of the emitting part 181.

Figure 4:
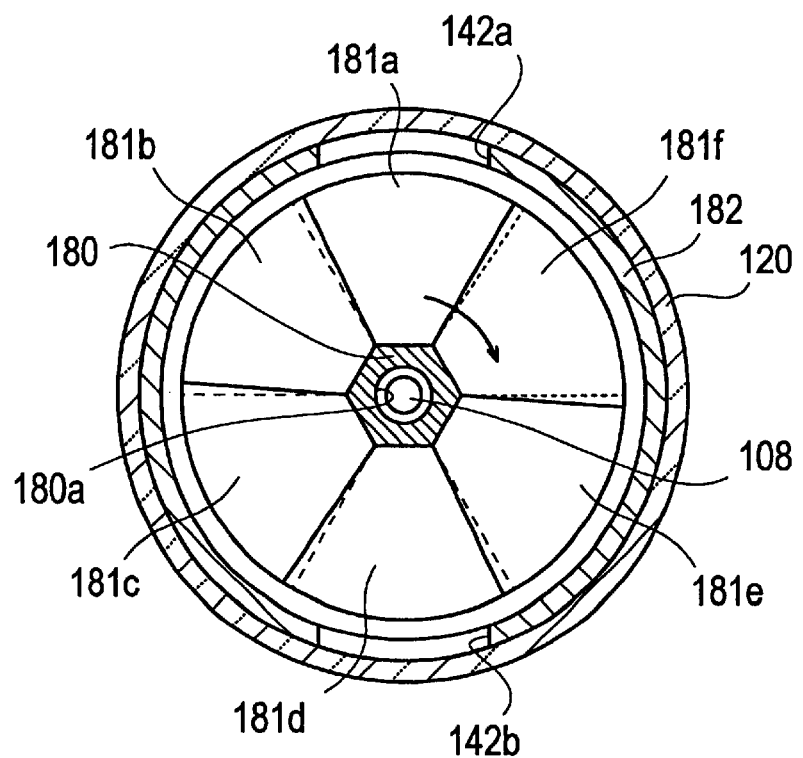
FIG. 4 is a cross-sectional view along the line B—B of the laser irradiation apparatus shown in FIG. 2.

As shown in FIG. 2 and FIG. 4, six emitting parts 181a through 181f are attached to the rotating shaft 180 in the first embodiment. The cross section of the part of the rotating shaft 180 where the emitting part 181 is to be attached is formed in a hexagonal shape. Emitting parts 181 are provided along the longitudinal direction of the rotating shaft 180 at a specific distance, e.g., 4 mm, apart from each other. Each emitting part 181 is located on each face of the hexagonal cross section, i.e., different positions along the circumferential direction of the rotating shaft 180. As is obvious from FIG. 4, each emitting part 181 is formed in a fan-shape. The edge that extends in the radial direction of each emitting part 181 is overlapping those of the adjacent emitting parts 181when seen from the axial direction.

When the emitting part 181a is reflecting the laser rays guided by the optical fiber 103a upward in the drawing, the emitting part 181d is reflecting the laser rays guided by the optical fiber 103b downward in the drawing. When the rotating shaft 180 rotates 180 degrees from this condition in the clockwise direction shown with an arrow in FIG. 4, the emitting part 181d reflects the laser rays guided by the optical fiber 103a upward, and the emitting part 181a reflects the laser rays guided by the optical fiber 103b downward. Thus, each emitting part 181a–181f reflects the laser rays in at different positions along the circumferential direction of the rotating shaft 180 toward different direction (up or down in the example shown in the drawing) as the rotating shaft 180 rotates.

The number of said "different positions" and their positional relations depend on the number of the optical fibers 103 installed and their relative positions. For example, if three optical fibers 103 are placed on the circumferential direction of the rotating shaft 180 an equal space (120 degrees) apart, the laser rays are reflected at three positions placed along the circumferential direction of the rotating shaft 180 an equal space (120 degrees) apart.

Each emitting part 181 comprises a reflective mirror coated with a reflective film 132 on a flat surface. The flat reflective film 132 can be formed by vapor depositing or plating a metal such as gold. A dielectric multi-layered film formed by vapor depositing reciprocally a high refraction rate dielectric substance such as $Al_2O_3$, $ZrO_2$, $TiO_2$ and $CeO_2$, and a low refraction rate dielectric substance such as $MgF_2$ and $SiO_2$ can be used as well for the same purpose. The thickness of the reflective film 132 is preferably about 0.2–1 μm. The laser rays transmitted through the optical fiber 103 are reflected by the reflective film 132 and emitted sideways from the fiber as shown with phantom lines in the drawing. The emitting parts 181 can be constituted of a polygon mirror.

Figure 5:
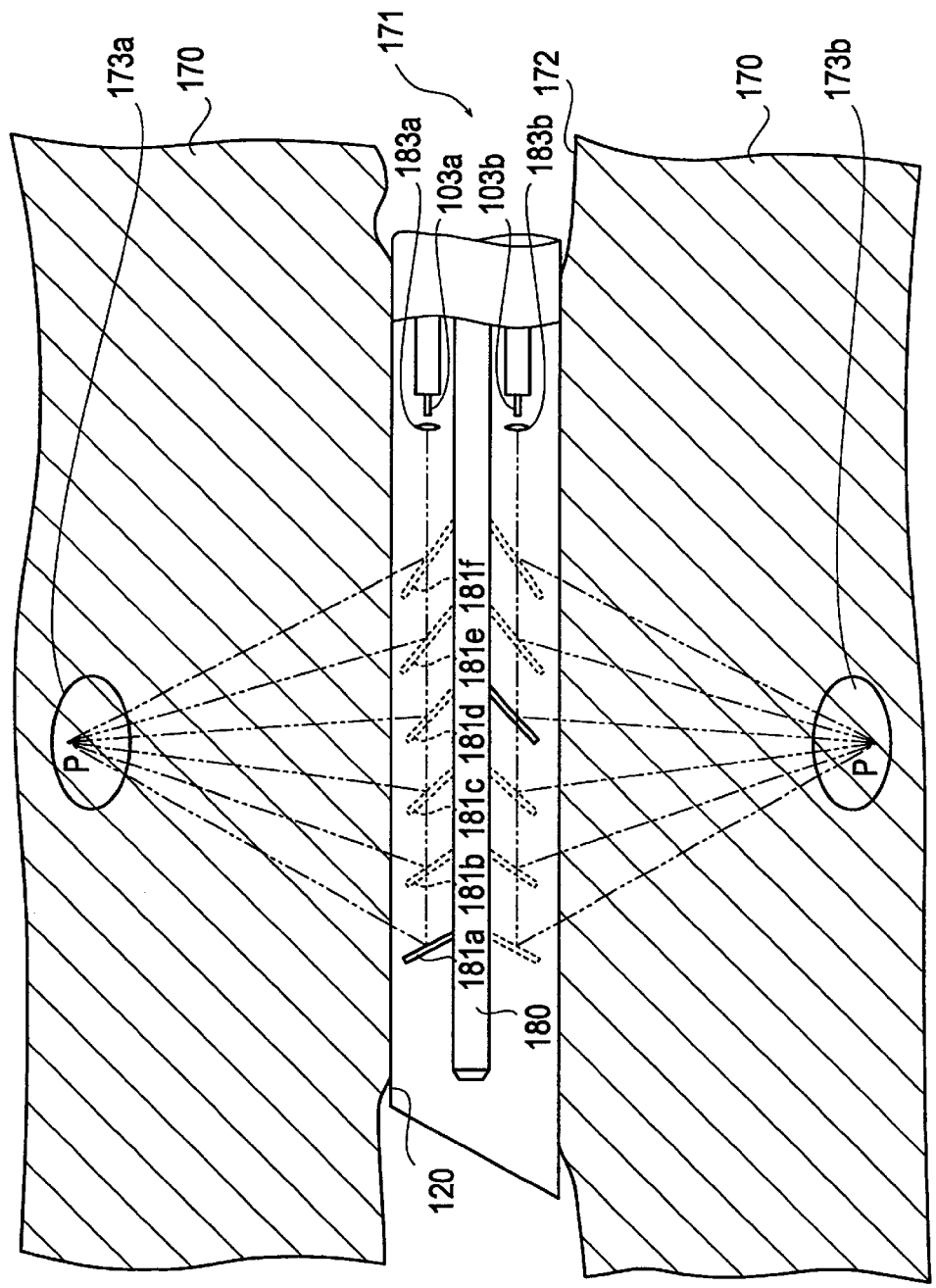
FIG. 5 is a schematic diagram showing an actual treatment to describe how the laser irradiation direction changes with the rotation of the rotating shaft.

With reference to FIG. 2 and FIG. 5, the slanting angle of each reflective mirror 181 relative to the longitudinal direction of the rotating shaft 180 is set in such a way that all the reflected laser rays converge on the particular area P when each reflective mirror cuts across the path of the laser rays.

Since the distance between the distal end 130 of the fiber and each reflective mirror 181 varies, the laser rays entering the reflective mirrors 181 have to be collimated rays in order that the reflected laser rays converge on the particular area P. Therefore, distal end lenses 183a and 183b are provided between the distal end 130 of the fiber and each reflective mirror 181, or preferably at the distal end 130 of the fiber, as optical devices to convert the laser rays provided by the optical fiber 103 to collimated rays.

The drive unit 105 has a motor 162, to which the electric power is supplied via an electric cable 161 built into a casing 160 as shown in FIG. 1, and a gearbox 163 that transmits the rotation of the motor 162 to the rotating shaft 180. The motor 162 can be used an induction motor, a servomotor, or a stepping motor. The drive unit 105 is constituted in such a way as to be able to change the rotating speed of the rotating shaft 180 arbitrarily within the range of 0.1–10 revolutions per second. It is also possible to constitute to have the drive unit 105 outside of the laser irradiation apparatus 100 and to connect the rotating shaft 180 with the drive unit 105 by means of a drive shaft.

In order to make it easier to understand, FIG. 5 shows a case where all of the reflective mirrors 181a–181f are either on the top or bottom side of the rotating shaft 180.

In FIG. 5, "170" shows the cross section of a prostate. The main body 101 is inserted in the urethra 171 and the protective cover 120 is closely contacting the urethra surface 172. It is also possible to have a balloon to press the protective cover 120 to the urethra surface 172.

The laser rays provided by the optical fiber 103a are reflected sequentially by reflective mirrors 181a–181f as the rotating shaft 180 rotates, and emitted sideways (preferably approximately perpendicular) relative to the longitudinal direction of the main body 101, or upward in the drawing. The laser rays provided by the optical fiber 103b are reflected sequentially by reflective mirrors 181a–181f downward in the drawing. The slanting angles of the reflective mirrors 181a–181f are such that the reflected laser rays converge on the particular area P. As a result, the reflected laser rays all converge on the target area 173 (collective name for 173a and 173b).

As the laser rays are irradiated while the rotating shaft 180 is rotating, the emitting position of the laser rays change constantly on the surface 172 of the vital tissues, or the surface layers below the target area 173a in the drawing and above the target area 173b in the drawing. Consequently, in the vicinity of surface, the photolepsy of the laser rays is littler and the energy provided by the laser rays is dispersed, thus generating little heat. Similarly, on the area above the target area 173a in the drawing and the area below the target area 173b in the drawing, the photolepsy of the laser rays is littler, thus generating little heat. On the other hand, on the target areas 173a and 173b located deep inside the vital tissue, the photolepsy of the laser rays is larger. Thus the energy provided by the laser rays concentrates on the target areas 173a and 173b and generates sufficient heat to heat and necrosis the legion.

Therefore, this technique solves the problem of the prior art that "the laser irradiation has to be limited to a level that does not affect the urethra surface 172 by heating" due to the fact that the laser rays were irradiated from a fixed laser irradiation part. In other words, the reflective mirrors 181a–181f that reflect the laser rays provided by the optical fibers 103a and 103b respectively essentially move in the longitudinal direction of the main body 101 in accordance with the rotation of the rotating shaft 180, thus converging all the reflected rays to the target area 173. As a result, the surrounding areas (normal tissues) other than the target area 173 are maintained at relatively low temperatures to protect from being affected by the laser rays. This laser irradiation apparatus 100 offers high curative effect to the patient because damage to the areas other than the target area 173 are prevented or reduced. It is particularly advantageous as the surface layer damages are prevented even when the target area 173 is located at a position deep inside the vital tissue.

The spacing between the adjacent reflective mirrors 181 and their slanting angles are adjusted in accordance with the diameter of the main body 101 and the depth of the target area 173 to be treated. In case of an apparatus for the benign prostatic hyperplasia treatment as in the first embodiment, the diameter of the main body 101 should preferably be approximately 4–10 mm and the depth of the particular area P should preferably be approximately 10–30 mm.

It is also possible to adjust the depth of the heated area by means of controlling the rotating speed of the rotating shaft 180. If the rotating speed is reduced, the irradiation time per unit area on the tissue surface 172 increases and the energy dispersion rate drops, thus increasing the surface temperature. Therefore, it is possible to expand the heated area toward the direction closer to the tissue surface 172 (or shallower). On the other hand, if the rotating speed is increased, the irradiation time on the tissue surface 172 becomes shorter, the heated area can be shrunken toward the direction deeper. Similarly, it is possible to change the position and the range of the target area 173 by properly adjusting the parameters such as the cooling water temperature and flow rate, laser output (W) and irradiation time.

Refer to FIG. 5, it is now described the operating procedure of the laser irradiation apparatus 100.

First, insert the main body 101 into a body cavity and locate the housing 182 on the surface layer in the vicinity of the target area 173, which is the legion, i.e., the location to be heated. It is preferable to confirm directly the position of the housing 182 by means of the endoscope 108. The target point position in the longitudinal direction of the body cavity can be adjusted by means of moving the main body 101 manually along the; longitudinal direction. The position of the target point in the circumferential direction of the body cavity can be adjusted by means of rotating the main body 101 manually.

When the positioning of the target point is completed, the operator selects the rotating speed of the rotating shaft 180 and other factors, in accordance with the severity of the prostatomegaly. Activate the laser generator, guide the generated laser rays through the optical fiber 103, and irradiate the target point with the laser rays reflected by the reflective mirror 181. Supply the cooling water to cool the urethra surface 172. The rotating shaft 180 should run at the speed of 0.1–10 revolutions per second, preferably 6 revolutions per second, driven by the drive unit 105. The optical axis of the laser rays changes continuously but always cross the target point. As a result, it is possible to heat and cure only the target area 173 located deep inside the tissue while protecting the vital tissue surface 172.

Next, change the target position by moving the main body 101 longitudinal and/or rotating it in the circumferential direction. When this position adjustment is completed, start the laser irradiation again. By repeating this operation as many times as needed, a relatively wide target area 173 can be heated.

The laser rays to be used on the laser irradiation apparatus 100 of the present embodiment can be of any kind as long as it can reach a certain depth of the vital tissue. However, the wavelength is preferably 750–1300 nm or 1600–1800 nm. Since laser rays with the wavelengths of 750–1300 nm or 1600–1800 nm provide excellent depth penetration capabilities and its energy is not absorbed much in the surface layer, so that it is possible to irradiate the target area (legion) lying in the deep area of the vital tissue more effectively.

Laser generators that generate laser rays of such ranges of wavelengths include gaseous laser generators such as He—Ne laser generators, solid lasers such as Nd—YAG lasers, and semiconductor lasers such as GaAlAs lasers.

The outside diameter of the main body 101 is not specified particularly as long as it can be inserted into the body cavity. However, the outside diameter of the main body 101 should be preferably 2–20 mm, or more preferably 3–8 mm.

Structural materials for the main body 101 can be a metal material such as stainless steel. Structural materials for the main body 101 can also be a polymer alloy containing at least one of the followings or a polymer material including multiple ingredients from the followings: polycarbonate; acryl; polyolefin such as polyethylene and polypropylene; ethylene-vinyl acetate copolymer (EVA); polyvinyl chloride; polyester such as polyethylene terephthalate and polybutylene terephthalate; polyamide; polyurethane; polystyrene; fluorocarbon resin; and acrylonitrile butadien styrene resin (ABS).

The surface of the main body 101 can be coated with lubricating materials such as hydrophilic polymer materials, silicon and fluorocarbon resin. They will reduce the friction of the main body surface, and make it smoother to insert it into body cavities. It is also possible to use a throwaway sheath to cover the main body and apply lubricating coating to the sheath surface. The potential shortcoming of deterioration of lubricating capability due to wear after multiple uses can be prevented by means of using a throwaway sheath.

Hydrophilic polymers that can be preferably used for lubrication coating include: carboxymethyl cellulose, polysaccharide, polyvinylalcohol, polyethylene oxide, polyacrylate soda, methylvinylether-maleic anhydride copolymer, and water soluble polyamide. Of these, methylvinylether-maleic anhydride copolymer is most preferable.

When a laser irradiation apparatus 100 equipped with a main body 101 coated with a hydrophilic polymer is used, the main body 101 can be immersed into physiological saline. This brings wetness of the surface layer of the main body 101 and the laser irradiation apparatus 100 comes to have lubricity. In other words, if the laser irradiation apparatus 100 has a surface layer containing a hydrophilic polymer, the friction resistance between the vital tissue and the laser irradiation apparatus 100 reduces. This reduces the burden of the patient and increases the safety. For example, insertion of the laser irradiation equipment 100 into a body cavity or its extraction from a body cavity or its transportation and rotation within a body cavity can be performed more smoothly.

The protective cover 120 that covers the housing 182 should be made of materials with excellent laser ray transmitting capabilities such as: acryl; polystyrene; polycarbonate; polyethylene; polypropylene; vinylidene chloride; and polyester such as polyethylene terephthalate and polybutylene terephthalate. It is not necessary to have the entire protective cover 120 be made of materials that are laser ray transmitting, but rather only the areas that correspond to the laser emitting window 142 have to be made of materials that are laser ray transmitting.

Instead of having the laser rays provided by both optical fibers 103a and 103b reflected as shown in the above, it is also possible to guide the laser rays by only one of the optical fibers, i.e., 103a (or 103b) and have only said laser rays be reflected depending on the position of the target area 173.

One example condition of the laser irradiation apparatus 100 used for treating the benign prostatic hyperplasia is as follows:

Effective length of the main body 101: 400 mm Diameter of the main body 101: 4–10 mm (preferably 7 mm)

Laser source: Semiconductor laser (wavelength: 700–1300 nm, 800–920 nm, 810 nm; continuous wave)

Optical fiber 103: Pure quartz fiber (core diameter: 300–800 μm, preferably 400 μm; numerical aperture NA=0.20)

Rotating speed of the rotating shaft 180: 0.1–10rev/sec (preferably 6 rev/sec)

Depth of the deep convergence point from the urethra: 10, 15, 20, 30 mm (preferably 20 mm)

Coolant: Distilled water (30–500 ml/min, preferably 250 ml/min; 0° C.)

Collimating lens: Rod lens, convex lens

Embodiment 2

In order to make it easier to understand, FIG. 6 schematically shows a case where all emitting parts are located above the rotating shaft. Members that have identical functions as those in the first embodiment are identified with the same codes and their descriptions are not repeated here.

The laser irradiation apparatus 200 of the second embodiment is different from that of the first embodiment in that the reflective mirrors 201 (collective name for 201a–201c) are provided in such a way as to be movable along the longitudinal direction of the rotating shaft 202. Moreover, it is equipped with a traveling unit 203 that makes each emitting part 201 travel along the longitudinal direction of the rotating shaft 202.

More specifically, the main body 101 is provided with only one optical fiber 204 in the second embodiment. The rotating shaft 202 held rotatably inside the main body 101 has a front end shaft 205, a rear end shaft 207, which is connected to the drive unit 105, and a middle shaft 206, which connects the front end shaft 205 with the rear end shaft 207. The front end shaft 205 and the middle shaft 206 are connected as if they constitute a cylinder and its liner and their separation is prevented by engaging parts 205a and 206a. The rear end shaft 207 and the middle shaft 206 are similarly connected as if they constitute a cylinder and its liner and their separation is prevented by engaging parts 207a and 206b. Keys or other similar devices (not shown) are provided between the front end shaft 205 and the middle shaft 206 as well as between the rear end shaft 207 and the middle shaft 206. When the rear end shaft 207 is rotatably driven by the drive unit 105, the middle shaft 206 and the front end shaft 205 drive together. The front end shaft 205 is supported to be free to rotate but its longitudinal movement is restricted by the housing 182.

The front end shaft 205 has a reflective mirror 201a, the middle shaft 206 has a reflective mirror 201b, and the rear end shaft 207 has a reflective mirror 201c. Each reflective mirror 201 is mounted at circumferentially different places on the rotating shaft 202 as in the case of the first embodiment.

Figure 7:
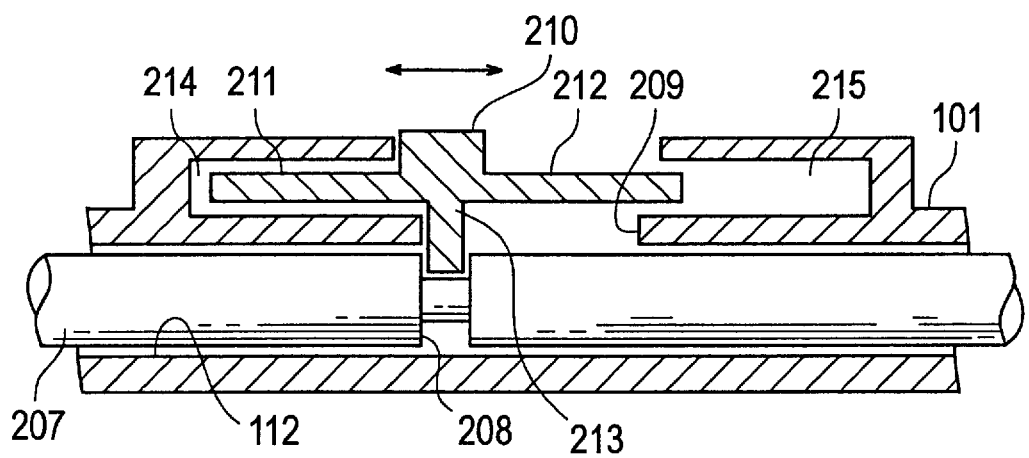
FIG. 7 is a cross section showing major components of a traveling unit that causes the emitting parts to travel in the longitudinal direction of the rotating shaft.

As shown in FIG. 7, the traveling unit 203 is so constituted as to be able to move the rear end shaft 207 axially by manual operation in order to move the reflective mirrors 201b and 201c in the longitudinal direction of the rotating shaft 202. The rear end shaft 207 is provided in the lumen 112 of the main body 101 free to travel back and forth freely and a concavity portion 208 is provided in the middle of the travel. The concavity portion 208 is exposed to a opening 209 formed axially on the main body 101. A slide lever 210 is provided at the opening 209 for manually moving the rear shaft 207. The slide lever 210 has guide plates 211 and 212 that extend along the axial direction of the main body 101, and an engaging protrusion 213 that extends along the radial direction of the main body 101. The guide plates 211 and 212 are guided by guide grooves 214 and 215 formed on the main body 101. The engaging protrusion 213 engages with the concavity portion 208 of the rear end shaft 207 through the opening 209.

When the slide lever 210 is moved toward the proximal side of the main body 101 shown as the right side of the drawing, the rear end shaft 207, which is connected to the slide lever 210 via the engaging protrusion 213 and the concavity portion 208, moves backward toward the proximal side. On the other hand, if the slide lever 210 is moved toward distal side of the main body 101 shown as the left side of the drawing, the rear end shaft 207, which is connected to the slide lever 210, moves forward toward the distal side.

Figure 6A:
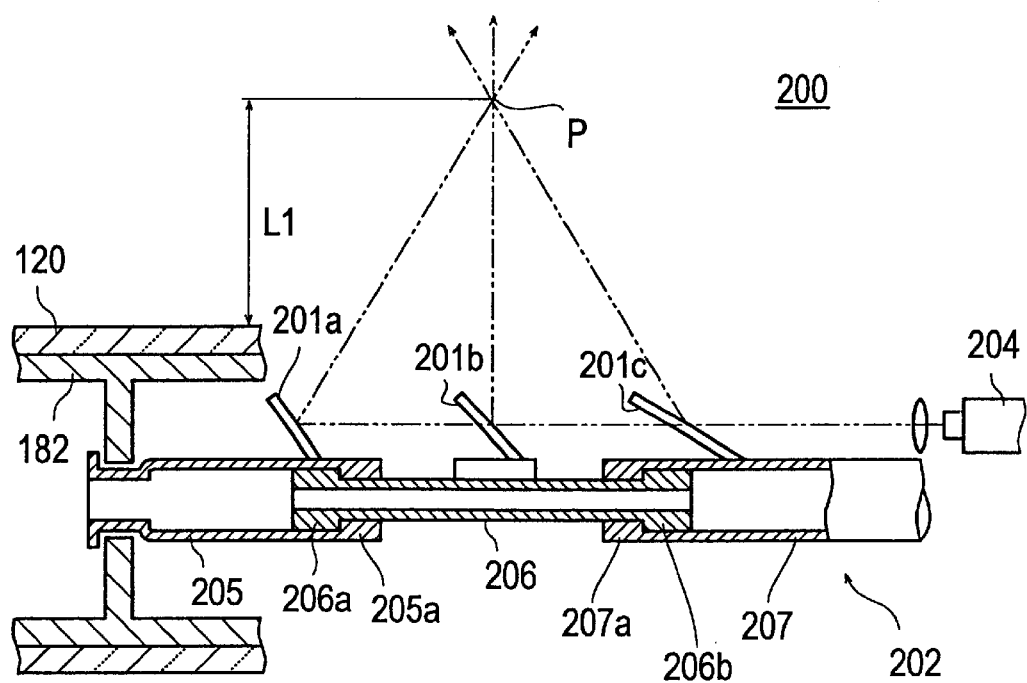
FIG. 6A and FIG. 6B are schematic cross sections showing the distal end of a laser irradiation apparatus according to a second embodiment, wherein FIG. 6A showing the condition when emitting parts are farthest apart from each other, while FIG. 6B showing the condition when emitting parts are closest to each other.
Figure 6B:
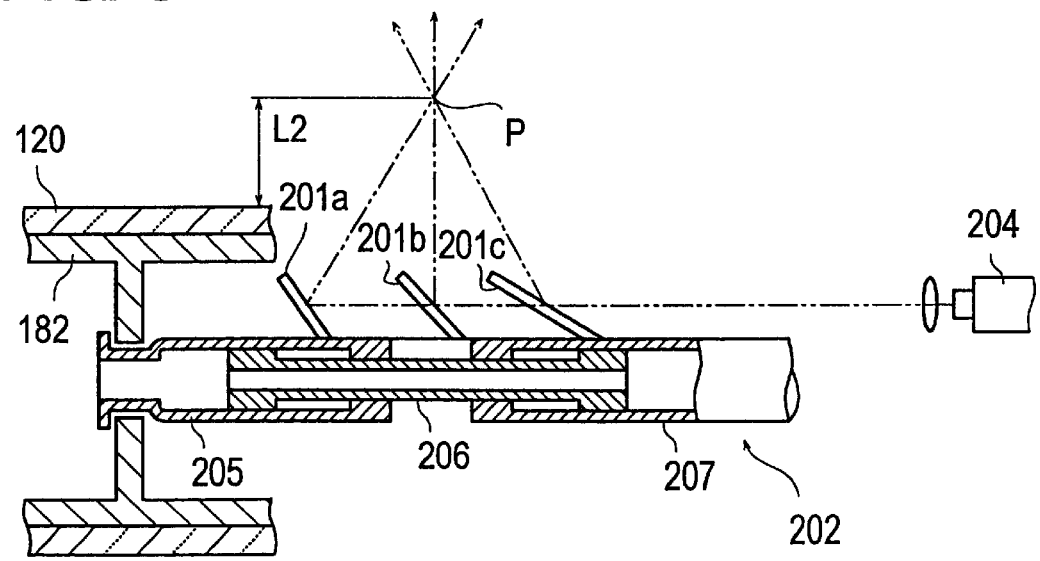

When the slide lever 210 is moved to the backward limit, the rotating shaft 202 is elongated as shown in FIG. 6A and the reflecting mirrors 201 become farthest apart from each other. On the other hand, if the slide lever 210 is moved to its forward limit, the middle shaft 206 advances deep into the front end shaft 205 and the rear end shaft 207, and the reflecting mirrors 201 become closest to each other as shown in FIG. 6B. Stoppers are attached to a base of the reflective mirrors 201b so that the distance between the reflective mirrors 201a and 201b is identical to the distance between the reflective mirrors 201b and 201c. The longitudinal position of the front end shaft 205 is restricted, so that the mirror 201a attached to it does not change its position. The relative distance between the reflective mirrors 201 is, for example, 15 mm when they are furthest apart from each other and 10 mm when they are closest to each other.

When the rotating shaft 202 is rotated and the laser rays are provided by the optical fibers 204 while the reflective mirrors 201 are furthest apart from each other as shown in FIG. 6A, the particular area P, where the reflected laser rays reflected by the reflective mirror 201 converge, becomes a deep spot far apart from the tissue surface 172 (depth L1). On the other hand, if the reflecting mirrors 201 are closest to each other, the particular area P, where the reflected laser rays converge, becomes a shallow spot in the vicinity of the tissue surface 172 (depth L2; L2<L1). Thus, it is possible to adjust the depth of the particular area P where the reflected laser rays converge while holding the angles of the reflecting mirrors 201 constant, enabling the treatment of the target area 173 at various depths.

Although the traveling unit 203 shown in the drawing is constituted to move the reflective mirrors 201 along the longitudinal direction of the rotating shaft 202 manually, but it can also be arranged to have a motor to drive the back and forth movement of the rear end shaft 207. Although a traveling unit shown here is constituted so as to switch the positions of the reflective mirrors 201 in two steps, the farthest apart and the closest, it can be constituted as a traveling unit with more switchable positions.

It is obvious that this invention is not limited to the particular embodiments shown and described above but may be variously changed and modified without departing from the technical concept of this invention.

What is claimed is:

1. Laser irradiation apparatus, comprising:

a long and slender main body;

a rotatable shaft that is held rotatably inside said main body;

at least one optical fiber which guides laser rays inside said main body, with the laser rays being emitted from an end of the at least one optical fiber, the end of the at least one optical fiber being exterior of the shaft;

multiple laser ray reflecting parts provided on said shaft and positioned relative to said at least one optical fiber to receive and reflect the laser rays guided by said optical fiber;

a motor operatively connected to the shaft for providing rotation to said shaft, wherein said multiple reflecting parts are arranged at different locations along a longitudinal direction and a circumferential direction of said shaft; and said multiple reflecting parts being caused by the rotation of said shaft to reflect the laser rays sequentially and irradiate the laser rays in the direction of vital tissues.

2. Laser irradiation apparatus in accordance with the claim 1, further comprising:

an endoscope that is inserted inside said rotating shaft.

3. Laser irradiation apparatus in accordance with the claim 1, wherein each reflecting part is coated with a reflective film to reflect the laser rays.

4. Laser irradiation apparatus in accordance with the claim 1, wherein positions where said reflecting parts reflect the laser rays moves axially as said rotating shaft rotates.

5. Laser irradiation apparatus in accordance with the claim 1, wherein said drive unit is capable of changing the rotating speed of said rotating shaft freely.

6. Laser irradiation apparatus in accordance with the claim 1, wherein each of said reflecting parts possesses a slanting angle relative to a longitudinal direction of said rotating shaft such that laser rays reflected from the reflecting parts converge.

7. Laser irradiation apparatus in accordance with the claim 1, wherein said rotating shaft is formed as a polygonal rod having a plurality of faces in an area where the multiple reflecting parts are provided, and each reflecting part is provided on one of the faces of said polygonal rod.

8. Laser irradiation apparatus in accordance with the claim 1, wherein multiple optical fibers are circumferentially arranged at different positions along the circumferential direction of said rotating shaft, and each reflecting part reflects the laser rays in different circumferential directions of said rotating shaft.

9. Laser irradiation apparatus in accordance with the claim 1, wherein said reflecting parts are provided movably along the longitudinal direction of said rotating shaft.

10. Laser irradiation apparatus in accordance with the claim 1, wherein distances between said multiple reflecting parts are adjustable.

11. Laser irradiation apparatus in accordance with the claim 1, wherein the laser rays converge at a point and a depth of the point where the laser rays are converged is adjustable.

12. Laser irradiation apparatus in accordance with the claim 1, wherein said reflecting parts are provided movably along the longitudinal direction of said rotating shaft, further comprising:

a traveling unit that causes said reflecting parts to travel along the longitudinal direction of said rotating shaft.

13. Laser irradiation apparatus in accordance with the claim 1, further comprises:

optical devices that convert the laser rays, which are guided by said optical fiber, into collimated rays.

14. Laser irradiation apparatus in accordance with the claim 1, further comprises:

a flow path for a coolant that cools surfaces which are irradiated by the laser rays.

* * * * *